United States Patent
Urich et al.

(10) Patent No.: US 9,216,035 B2
(45) Date of Patent: Dec. 22, 2015

(54) SURGICAL INSTRUMENT RINGING A TITANIUM NEEDLE WITH A NODE OF MINIMUM AMPLITUDE IN A SUBSTANTIALLY CYLINDRICAL PORTION OF THE NEEDLE

(76) Inventors: Alex Urich, Rancho Santa Margarita, CA (US); Armand Maaskamp, Coto De Casa, CA (US)

( * ) Notice: Subject to any disclaimer, the term of this patent is extended or adjusted under 35 U.S.C. 154(b) by 369 days.

(21) Appl. No.: 13/430,633

(22) Filed: Mar. 26, 2012

(65) Prior Publication Data

US 2013/0253557 A1    Sep. 26, 2013

(51) Int. Cl.
| | | |
|---|---|---|
| *A61F 9/00* | (2006.01) | |
| *A61B 17/3209* | (2006.01) | |
| *A61F 9/007* | (2006.01) | |
| *A61B 17/22* | (2006.01) | |

(52) U.S. Cl.
CPC .......... *A61B 17/3209* (2013.01); *A61F 9/00745* (2013.01); *A61B 2017/22018* (2013.01)

(58) Field of Classification Search
CPC ................. A61B 17/3209; A61B 2017/22018; A61F 9/00745
USPC ....... 606/169, 107; 604/22; 600/564
See application file for complete search history.

(56) References Cited

U.S. PATENT DOCUMENTS

| | | | | |
|---|---|---|---|---|
| 5,062,827 A | * | 11/1991 | Wiksell | 604/22 |
| 5,112,300 A | * | 5/1992 | Ureche | 604/22 |
| 5,123,903 A | * | 6/1992 | Quaid et al. | 604/22 |
| 5,171,387 A | * | 12/1992 | Wuchinich | 156/73.3 |
| 5,176,677 A | * | 1/1993 | Wuchinich | 606/46 |
| 5,180,363 A | * | 1/1993 | Idemoto et al. | 604/22 |
| 5,213,569 A | * | 5/1993 | Davis | 604/22 |
| 5,255,669 A | * | 10/1993 | Kubota et al. | 601/3 |
| 5,269,297 A | * | 12/1993 | Weng et al. | 606/128 |
| 5,391,144 A | * | 2/1995 | Sakurai et al. | 604/22 |
| 2005/0187514 A1 | * | 8/2005 | Rabiner et al. | 604/22 |
| 2009/0069712 A1 | * | 3/2009 | Mulvihill et al. | 600/564 |
| 2009/0143796 A1 | * | 6/2009 | Stulen et al. | 606/169 |

* cited by examiner

*Primary Examiner* — Tuan V Nguyen
*Assistant Examiner* — Tin Nguyen
(74) *Attorney, Agent, or Firm* — Kenneth Althshuler

(57) ABSTRACT

A surgical instrument and method, for example to accomplish phacoemulsification, are disclosed. The surgical instrument includes a handpiece that has a piezoelectric transducer, and a titanium needle having a free distal tip and a supported end that is attached to the handpiece. The titanium needle has a substantially cylindrical portion with an outer diameter in the range 0.5 mm to 1.5 mm and a length in the range 12 mm to 37 mm. A circuit drives the piezoelectric transducer to periodically longitudinally expand and longitudinally contract at a driving frequency. The driving frequency is selected to ring the titanium needle with a standing wave that is characterized by longitudinal expansion and longitudinal contraction, the standing wave having a distal node of minimum amplitude in the substantially cylindrical portion.

20 Claims, 2 Drawing Sheets

SURGICAL INSTRUMENT RINGING A TITANIUM NEEDLE WITH A NODE OF MINIMUM AMPLITUDE IN A SUBSTANTIALLY CYLINDRICAL PORTION OF THE NEEDLE

FIELD OF THE INVENTION

The present invention relates generally to the field of medical devices used in surgery, and more particularly to tools and methods used in phacoemulsification procedures.

BACKGROUND

Needles that are actuated at ultrasonic frequencies may be used in various contemporary surgical procedures. For example, the lens of a human eye may develop a cataracteous condition that affects a patient's vision. Cataracteous lenses are sometimes removed and replaced in a procedure commonly referred to as phacoemulsification. Phacoemulsification procedures are typically performed with a hand piece that actuates a needle at ultrasonic frequencies. The needle is inserted through an incision in the cornea up to a desired insertion depth, and then the ultrasonic actuation is used to break the lens within the lens capsule of the eye. The broken lens may be removed through an aspiration line that is coupled to the hand piece, drawing irrigation fluid and aspirated tissue from a hollow passage through the needle.

Phacoemulsification procedures are more likely to be successful if cavitation of the irrigation fluid is limited or controlled to prevent interference with acceptable aspiration. Phacoemulsifacation procedures are also more likely to be successful if heating of tissue at the incision in the cornea, which may be caused by actuation of the needle, is prevented or limited. Therefore, there is a need in the art for an improved apparatus and/or method for ultrasonic actuation of a needle attached to the handpiece of a surgical instrument.

SUMMARY

A surgical instrument and method, for example to accomplish phacoemulsification, are disclosed. The surgical instrument includes a handpiece that has a piezoelectric transducer, and a titanium needle having a free distal tip and a supported end that is attached to the handpiece. The titanium needle has a substantially cylindrical portion with an outer diameter in the range 0.5 mm to 1.5 mm and a length in the range 12 mm to 37 mm. A circuit drives the piezoelectric transducer to periodically longitudinally expand and longitudinally contract at a driving frequency. The driving frequency is selected to ring the titanium needle with a standing wave that is characterized by longitudinal expansion and longitudinal contraction, the standing wave having a distal node of minimum amplitude in the substantially cylindrical portion.

DETAILED DESCRIPTION

Figure 1:
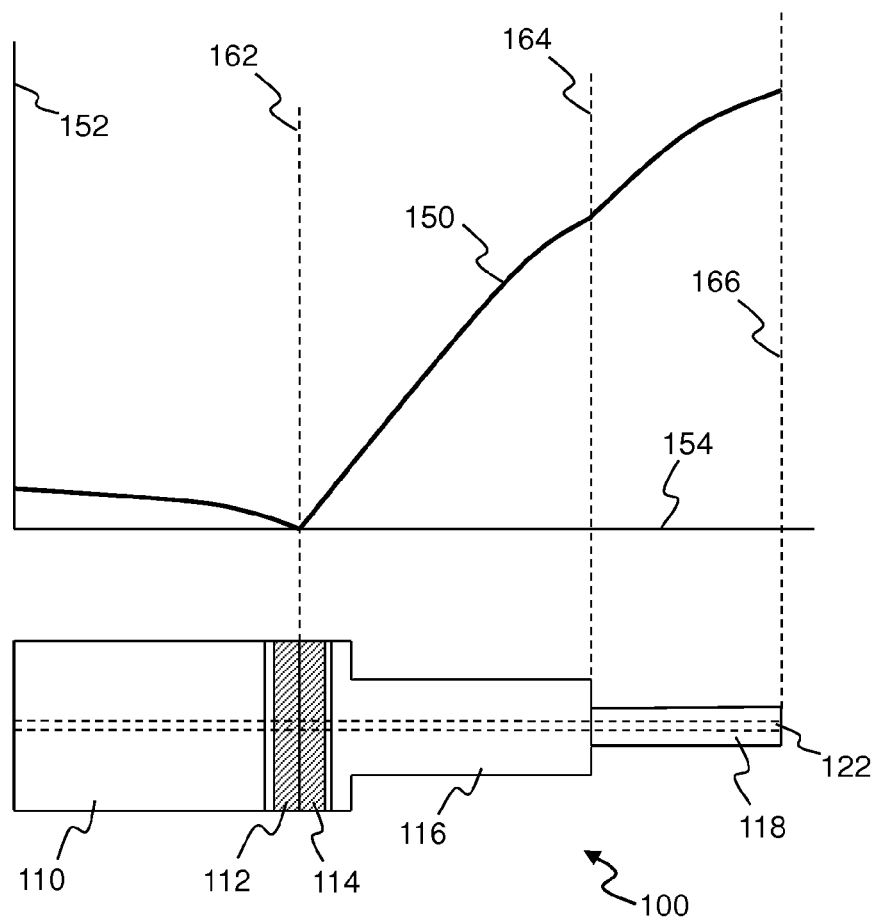
FIG. 1 depicts a handpiece of a surgical instrument driving conventional 40 kHz longitudinal vibration of a phacoemulsification needle.

During an ultrasonic phacoemulsification surgical procedure, a cataracteous lens may be broken into particles by the combined cutting action of an ultrasonically vibrating needle tip and cavitation effects. The vibration may provide penetration of the needle into lens tissue, while the cavitation may help emulsify or disintegrate lens tissue into small particles that can be aspirated through a narrow tube. Cavitation can occur because the needle compresses and expands along its longitudinal axis, thus generating longitudinal waves in the surrounding fluid. Unlike torsional and shear waves, longitudinal waves may propagate well in fluids.

The effectiveness of a surgical instrument for phacoemulsification depends on the rate at which tissue is removed, which may be substantially affected by cavitation since cavitation may reduce partial or total occlusions of the needle. On the other hand, a particle engaged with the needle by vacuum may partially disintegrate if the ultrasonic energy causes high cavitation. In this case, the surgeon may lose the particle and additional maneuvers may be necessary to reengage. Retention of tissue particles in engagement with the needle is desirable and may be referred to as "followability." To improve followability, reduced cavitation during phacoemulsification may be advantageous.

One way to reduce cavitation is to excite the needle to vibrate torsionally rather than longitudinally, so that the needle tip alternately rotates clockwise and counter-clockwise in relation to its longitudinal axis. Torsional vibrations do not readily propagate as waves in fluid, so that cavitation effects are substantially reduced. However a needle tip that is vibrating purely torsionally may too easily core into the lens material without sufficient disintegration of tissue into particles, which, in turn, may too frequently lead to total occlusions in the needle.

According to one of the embodiments of the present invention disclosed herein, followability may be enhanced instead by longitudinally ringing a needle at a carefully selected and substantially higher frequency than has been used previously for phacoemulsification. Most preferably, the ringing frequency is chosen so that the phacoemulsification needle length corresponds to approximately three quarter vibration wavelengths. Such a higher ultrasonic frequency, in combination with the proper length of the needle, may lead to reduced heating of tissue at the incision in the cornea, and may generate larger numbers but smaller sized cavitation bubbles per unit volume. The energy delivered by a cavitation bubble is related to the bubble radius, which in turn is inversely related to the frequency of vibration. For example, a bubble size generated by a 40 KHz wave may be approximately 41 μm, while being only 7.6 μm at 215 KHz. When more and smaller bubbles are generated, cavitation patterns may be more uniformly distributed over the cutting area, which, in turn, may enhance followability relative to phacoemulsification needles operating with conventional longitudinal ultrasonic vibrations.

A handpiece 100 for longitudinal vibration of a phacoemulsification needle 118, operating conventionally at 40 KHz, is shown in FIG. 1. The handpiece 100 includes a back cylinder 110 and a front cylinder 116 compressing a pair of piezoelectric crystals 112, 114 through a central bolt (not shown). The wavelength λ of a longitudinally ringing structure is given by the formula λ=c/f where c is the speed of sound through the structure's material and f is the frequency of operation. Titanium material exhibits a speed of sound that is approximately 4,876,800 mm/sec. Hence, a titanium structure longitudinally vibrating at a conventional ultrasonic frequency of 40 KHz (40000 Hz) has a wavelength of (4,876,800 mm/s)/(40,000 Hz)=122 mm.

In FIG. 1, the combined length of the front and back cylinders 110, 116 is approximately ½ wavelength during conventional operation, with a node of zero vibration amplitude at a location 162 at the interface between the two piezoelectric crystals 112, 114. For that reason, the handpiece 100 may be referred to as a "half-wavelength horn." The handpiece 100 (and needle 118) has a longitudinal through-hole that is necessary to evacuate fluid and tissue removed from the eye.

FIG. 1 is not drawn to scale, so that the phacoemulsification needle 118 may be more clearly depicted as a hollow cylinder. The needle 118 may comprise titanium and be attached to the handpiece 100 using threads (not shown). The length of the needle 118 has a very small cross-sectional area and has a length that is less than ¼ wavelength (30.5 mm at 40 kHz), for example 17 mm. The mass of the needle 118 is also very small when compared with the mass of the handpiece 100. Consequently the needle does not dramatically change the dynamic resonance characteristics of the handpiece 100. The needle 118 is hollow to include a narrow tubular passage 122 therethrough. The tubular passage 122 continues through the entire handpiece 100 so that fluid and tissue can be aspirated through the needle 118 to an aspiration tube that is connected to the handpiece and provides sub-ambient pressure to the narrow tubular passage 122.

The cross sectional area of the front cylinder 116 of the handpiece 100 is smaller than the cross section area of the back cylinder 110, in order to provide displacement magnification as shown in the graph 150 in the upper portion of FIG. 1. Specifically the displacement at the rightmost extent 164 of the front cylinder 116 may be about 20 times the displacement at the leftmost edge 152 of the rear cylinder 110. Note that the vertical axis 152 of the graph 150 represents displacement amplitude (increasing upwards). The horizontal axis 154 of the graph 150 represents the longitudinal coordinate along the length of the handpiece 100 and needle 118. Longitudinal strain in the needle 118 marginally increases displacement plotted in graph 150, though the entire needle 118 longitudinally translates. For example, the displacement at the location 166 of the distal end of the needle 118 is somewhat greater than the displacement at the rightmost extent 164 of the front cylinder 116. Note that there is no location of zero vibration (i.e. nodal point) along the length of the needle 118.

Figure 2:
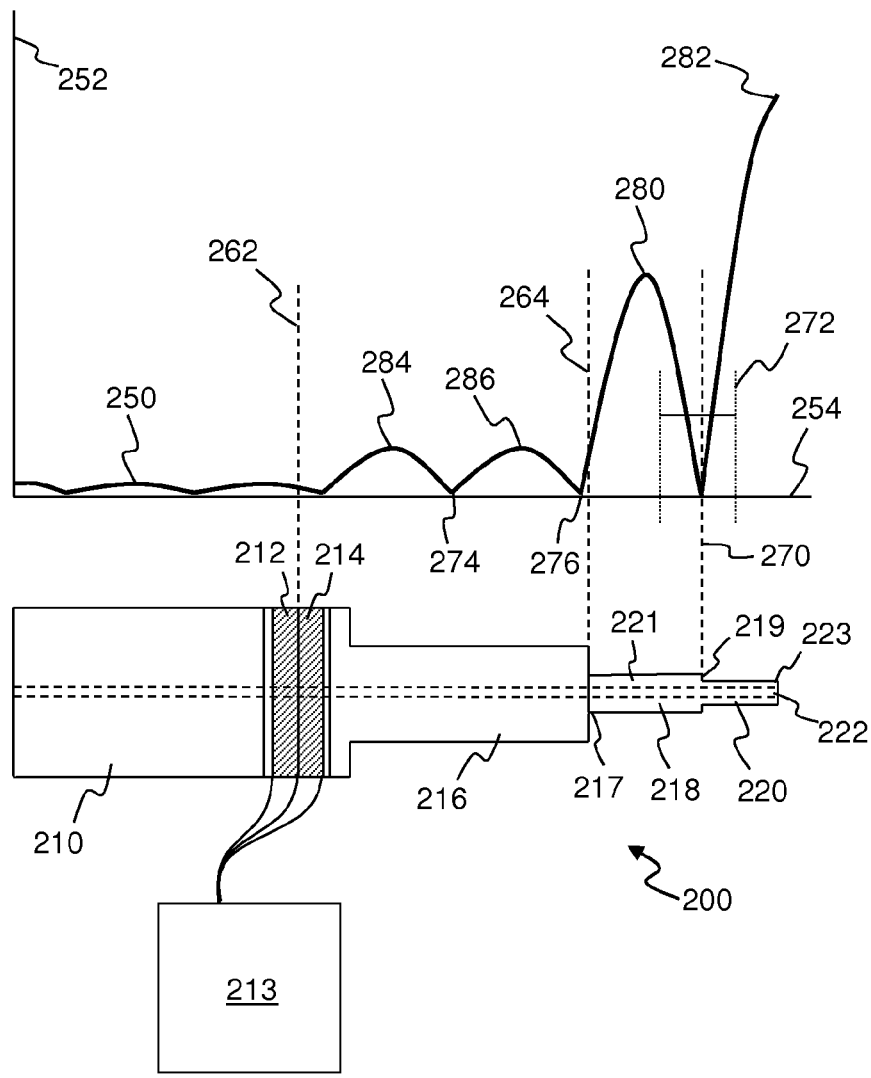
FIG. 2 depicts a handpiece of a surgical instrument ringing a phacoemulsification needle according to an embodiment of the present invention.

FIG. 2 depicts a surgical instrument comprising a handpiece 200 ringing a phacoemulsification needle 218 according to an embodiment of the present invention. The handpiece 200 includes a piezoelectric transducer 212, 214. Preferably the piezoelectric transducer comprises a sandwich structure of two piezoelectric elements 212, 214 which meet at an interface location 262. The piezoelectric elements 212, 214 may comprise piezoelectric ceramics or crystals, preloaded to be in compression by a bolt in tension, for example.

The handpiece 200 may optionally include a back cylinder 210 that may have a back cylinder outer diameter that is preferably in the range 9.5 mm to 13 mm. The back cylinder 210 may comprise stainless steel, for example. The handpiece 200 may also optionally include a front cylinder 216 that may have a front cylinder outer diameter that is preferably in the range 3.5 mm to 6.5 mm. In this case, the piezoelectric transducer 212, 214 is preferably disposed between the back cylinder 210 and the front cylinder 216.

The surgical instrument depicted in FIG. 2 includes the handpiece 200 and the phacoemulsification needle 218. The phacoemulsification needle 218 preferably comprises titanium and has a free distal tip 223 and a supported end 217 that is attached to the handpiece 200. For example, the supported end 217 of the needle 218 may include external threads that mate with internal threads of a corresponding hole in the front cylinder 216. The front cylinder 216 may also comprise titanium, for example to match the speed of sound in the titanium needle 218 and thereby reduce acoustic reflections at the interface between the front cylinder 216 and the titanium needle 218.

In the embodiment of FIG. 2, the needle 218 is substantially cylindrical, with an outer diameter in the range 0.5 mm to 1.5 mm and a length in the range 12 mm to 37 mm, the length being defined along a longitudinal axis of the needle 218 (i.e. parallel to graph axis 254). In this context "cylindrical" does not necessarily mean cylindrical with a circular or annular cross section. Rather, any closed hollow extruded shape may be used (e.g. a closed hollow square cross-section). However, an annular cross-section having circular inner and outer peripheries may be preferred for manufacturability. The needle 218 is hollow to include a narrow tubular passage 222 therethrough. The tubular passage 222 may continue through the handpiece 200 so that fluid and tissue may be aspirated through the needle 218 to an aspiration tube that is connected to the handpiece and provides sub-ambient pressure to the narrow tubular passage 222.

In the embodiment of FIG. 2, the needle 218 optionally includes a shoulder 219 where the outer diameter of the needle 218 changes. The needle 218 includes a first substantially cylindrical portion 220 between the shoulder 219 and the free distal tip 223, and a second substantially cylindrical portion 221 between the shoulder 219 and the supported end 217. In this case, the shoulder 219 is preferably disposed between 5 mm to 8 mm from the free distal tip 223. The outer diameter of the needle 218 is preferably less in the first substantially cylindrical portion 220 than in the second substantially cylindrical portion 221, as such inequality may advantageously amplify the ringing amplitude in the first substantially cylindrical portion 220.

The surgical instrument depicted in FIG. 2 includes a circuit 213 that provides an oscillating voltage to the piezoelectric transducer 212, 214 in the handpiece 200, the voltage oscillating at a driving frequency that rings the titanium needle 218 with a standing wave that is characterized by longitudinal expansion and longitudinal contraction. In certain embodiments, the total length of the needle 218 (including both substantially cylindrical portions 220, 221) is preferably in the range 13 mm to 38 mm, and the frequency with which the circuit 213 drives the piezoelectric transducer 212, 214 is preferably in in the range 95 kHz to 290 kHz. For example, the total length of the needle 218 may be approximately 17 mm, and the driving frequency may be approximately 215 kHz.

Such dimensional ranges and driving frequencies may advantageously result in 3 quarter wavelengths of the longitudinal standing wave lying along the needle 218 if it is a titanium needle of 17 mm total length. This can be verified by referring again to the formula $\lambda=c/f$. Specifically, according to this formula the wavelength of the standing longitudinal wave in a titanium needle would be (4,876,800 mm/s)/215,000 Hz)=22.7 mm. Hence, approximately ¾ wavelengths would lie along a needle length of 17 mm.

An example of the amplitude of the longitudinal expansion and longitudinal contraction along the handpiece 200 and the needle 218, according to an embodiment of the present invention, is plotted versus longitudinal position in the graph 250 that appears above the handpiece 200 in FIG. 2. The vertical axis 252 of the graph 250 represents displacement amplitude (increasing upwards). The horizontal axis 254 of the graph 250 represents the longitudinal coordinate along the length of the handpiece 200 and the needle 218.

In the embodiment of FIG. 2, the standing wave shown in graph 250 preferably has a distal node of minimum amplitude at a node location 270 on the substantially cylindrical needle 218. That is depicted on the graph 250 as a minimum point at the node location 270. Unlike conventional ultrasonic phacoemulsification (e.g. like that shown in FIG. 1), the portion of the needle 118 that is most likely to contact the incision in the cornea, may be in a region 272 that includes a minimum node in the standing wave of vibration, and therefore experiences a much lower motion than does the distal tip 223. In certain embodiments, this may advantageously reduce heating of the tissue at and near the incision in the cornea.

In certain embodiments, including certain embodiments that lack any shoulder 219, the reduced corneal incision heating advantage may be obtained by the distal node of minimum amplitude (at node location 270) being preferably disposed between 5 mm to 8 mm from the free distal tip 223. Although in the embodiment of FIG. 2 the shoulder 219 is depicted as being immediately adjacent the distal node of minimum amplitude (at node location 270), there is no requirement for that, and indeed in certain embodiments it is preferred that they not be at the same longitudinal location. For example, in certain embodiments, it is preferred that the distal node of minimum amplitude (at node location 270) be disposed more distally (to the right in FIG. 2) than the shoulder 219.

In the embodiment of FIG. 2, the standing wave shown in graph 250 has a proximal node of minimum amplitude 276 near or adjacent the supported end 217. That is depicted as a minimum point on the graph 250, just to the left of the location 264. Note that the proximal node of minimum amplitude 276 is not the same as the distal node at node location 270, and it does not serve the same purposes as described for the distal node at node location 270. Also in the embodiment of FIG. 2, the standing wave shown in graph 250 may have a distal anti-node 282 of maximum amplitude at the free distal tip 223, so that high displacement amplitude at the distal tip 223 can enhance tissue penetration by the distal tip 223.

Other nodes (e.g. node 274) may exist in the displacement amplitude graph along the front cylinder 216, but these are not the same as the distal node at node location 270, nor do they serve the same purposes as described for the distal node at node location 270. Another anti-node 280 may exist in the substantially cylindrical portion of the needle 218, but it does not serve the same purpose as does the distal anti-node 282 of maximum amplitude at the free distal tip 223. However, in certain embodiments, the existence and location of the anti-node 280 is an expected consequence of the desired placement of the distal node of minimum amplitude at a node location 270 on the substantially cylindrical needle 218 (as described in previous paragraphs). Other anti-nodes (e.g. anti-nodes 284, 286) may exist in the displacement amplitude graph along the front cylinder 216, but these are not the same as the distal anti-node 282 of maximum amplitude at the free distal tip 223, nor do they serve the same purpose as does the distal anti-node 282 of maximum amplitude at the free distal tip 223.

In the foregoing specification, the invention is described with reference to specific exemplary embodiments, but those skilled in the art will recognize that the invention is not limited to those. It is contemplated that various features and aspects of the invention may be used individually or jointly and possibly in a different environment or application. The specification and drawings are, accordingly, to be regarded as illustrative and exemplary rather than restrictive. For example, the word "preferably," and the phrase "preferably but not necessarily," are used synonymously herein to consistently include the meaning of "not necessarily" or optionally. "Comprising," "including," and "having," are intended to be open-ended terms.

What is claimed is:

1. A surgical instrument comprising:
a handpiece that includes a piezoelectric transducer;
a titanium needle having a free distal tip and a supported end having a supported end structure that is attached to the handpiece, the titanium needle having a substantially cylindrical portion between the supported end structure and the free distal tip, the cylindrical portion having an outer diameter in the range 0.5 mm to 1.5 mm and a length in the range 12 mm to 37 mm, the length being defined along a longitudinal axis of the titanium needle;
a circuit driving the piezoelectric transducer to periodically longitudinally expand and longitudinally contract at a driving frequency that rings the titanium needle with a standing wave that is characterized by longitudinal expansion and longitudinal contraction, the standing wave consisting of one node of minimum amplitude residing in the substantially cylindrical portion away from the supported end structure and the free distal tip.

2. The surgical instrument of claim 1 wherein the standing wave has a proximal node of minimum amplitude adjacent the supported end.

3. The surgical instrument of claim 1 wherein the standing wave has a distal anti-node of maximum amplitude at the free distal tip.

4. The surgical instrument of claim 1 wherein the node of minimum amplitude is disposed between 5 mm to 8 mm from the free distal tip.

5. The surgical instrument of claim 1 wherein the length is the range 13 mm to 38 mm, and the driving frequency is in the range 95 kHz to 290 kHz.

6. The surgical instrument of claim 5 wherein the length is approximately 17 mm, and the driving frequency is approximately 215 kHz.

7. The surgical instrument of claim 1 wherein the substantially cylindrical portion includes a shoulder where the outer diameter changes, the outer diameter being less between the shoulder and the free distal tip than it is between the shoulder and the supported end.

8. The surgical instrument of claim 7 wherein the shoulder is disposed between 5 mm to 8 mm from the free distal tip.

9. The surgical instrument of claim 1 wherein the handpiece further includes a stainless steel back cylinder having back cylinder outer diameter in the range 9.5 mm to 13 mm.

10. The surgical instrument of claim 9 wherein the handpiece further includes a titanium front cylinder having front cylinder outer diameter in the range 3.5 mm to 6.5 mm, the piezoelectric transducer being disposed between the stainless steel back cylinder and the titanium front cylinder, the titanium needle being attached to the titanium front cylinder.

11. A surgical instrument comprising:
a phacoemulsification device possessing a handpiece and a titanium needle;
the handpiece that includes a piezoelectric transducer;
the titanium needle having a free distal tip and a supported end that is attached to the handpiece, the titanium needle having a substantially cylindrical portion between the supported end and the free distal tip;
a circuit driving the piezoelectric transducer to periodically longitudinally expand and longitudinally contract at a driving frequency that rings the titanium needle with a standing wave that is characterized by longitudinal expansion and longitudinal contraction, the standing wave consisting a single node of minimum amplitude in the substantially cylindrical portion, the node of minimum amplitude does not include the supported end.

12. The surgical instrument of claim 11 wherein the standing wave has a proximal node of minimum amplitude adjacent the supported end.

13. The surgical instrument of claim 11 wherein the standing wave has a distal anti-node of maximum amplitude at the free distal tip.

14. The surgical instrument of claim 11 wherein the length is the range 13 mm to 38 mm, and the driving frequency is in the range 95 kHz to 290 kHz.

15. The surgical instrument of claim 11 wherein approximately three-quarters of the standing wave lies along the substantially cylindrical portion between the supported end and the free distal tip.

16. A surgical instrument comprising:
a handpiece that includes a piezoelectric transducer;
a titanium needle including a supported end structure and a hollow cylinder that extends from the supported end structure terminating at a free distal tip, the titanium needle attached to the handpiece via the supported end structure;
a circuit driving the piezoelectric transducer to periodically longitudinally expand and longitudinally contract at a driving frequency that rings the titanium needle with a standing wave that is characterized by less than a full wavelength that lies along the hollow cylinder, the standing wave having only a single distal node of minimum amplitude in the hollow cylinder between the free distal tip and the supported end structure.

17. The surgical instrument of claim 16 wherein the hollow cylinder includes a shoulder where an outer diameter changes, the outer diameter being less between the shoulder and the free distal tip than it is between the shoulder and the supported end structure.

18. The surgical instrument of claim 16 wherein the standing wave is approximately a three-quarter vibration wavelength along the hollow cylinder.

19. The surgical instrument of claim 16 wherein the handpiece and the titanium needle are configured for phacoemulsification procedures to a human eye.

20. The surgical instrument of claim 19 wherein the titanium needle is adapted to penetrate the human eye essentially only as far as the single distal node of minimum amplitude.

* * * * *